(12) United States Patent
Billack et al.

(10) Patent No.: US 8,426,452 B2
(45) Date of Patent: *Apr. 23, 2013

(54) PROCESS FOR THE TREATMENT AND PREVENTION OF DISEASES CAUSED BY FUNGI

(76) Inventors: Blase Christopher Billack, Clifton, NJ (US); Aneta Marta Billack, Clifton, NJ (US)

( * ) Notice: Subject to any disclaimer, the term of this patent is extended or adjusted under 35 U.S.C. 154(b) by 916 days.

This patent is subject to a terminal disclaimer.

(21) Appl. No.: 12/378,323

(22) Filed: Feb. 17, 2009

(65) Prior Publication Data

US 2009/0239913 A1 Sep. 24, 2009

Related U.S. Application Data

(60) Provisional application No. 61/065,833, filed on Feb. 19, 2008.

(51) Int. Cl.
*A01N 43/64* (2006.01)
*A61K 31/41* (2006.01)

(52) U.S. Cl.
USPC ......................................................... 514/359

(58) Field of Classification Search .................... 514/359
See application file for complete search history.

(56) References Cited

PUBLICATIONS

Muesh et al. (Chemistry of Biologically Important Synthetic Organoselenium CompoundsChem. Rev. 2001, 101, 2125-2179).*

* cited by examiner

*Primary Examiner* — Sreeni Padmanabhan
*Assistant Examiner* — Layla Soroush

(57) ABSTRACT

The subject invention is directed to the treatment of infections caused by fungi which are resistant to standard antifungal drugs such as fluconazole. The treatment method involves administering to the sufferer an effective amount of an agent that suppresses the activity of the fungal (H+)-ATPase pump (Pma1p). Such agents may take the form of: a) 2-phenyl-1,2-benzisoselenazol-3(2H)-one, commonly referred to as ebselen and depicted by Formula I, or b) 2-phenyl-1,2-benzisoselenazol-3(2H)-one 1-oxide, commonly referred to as ebselen se-oxide and depicted by Formula II, or pharmaceutically acceptable salts thereof. Opportunistic fungal infections include those which are systemic and those which are superficial and are caused by species of fungi belonging to the genus *Candida, Aspergillus, Pneumocystis, Tinea, Blastomyces, Cryptococcus, Histoplasma, Sporotrichum, Malassezia, Hansenula, Rhodotorula, Trichosporon*, as well as others.

6 Claims, 6 Drawing Sheets

| | Atomic composition, chemical and generic names of the preferred benzisoselenazol-bearing compounds described herein | | |
|---|---|---|---|
| formula | atomic composition | chemical name(s) | generic name |
| I | $C_{13}H_9NOSe$ | 2-phenyl-1,2-benzisoselenazol-3(2H)-one | ebselen |
| II | $C_{13}H_9NO_2Se$ | 2-phenyl-1,2-benzisoselenazol-3(2H)-one 1-oxide; 2-phenyl-1,2-benzisoselenazol-1,3-dione | ebselen se-oxide |

FIG 1

Growth inhibitory effect of ebselen, ebselen se-oxide and standard antifungals upon fluconazole-sensitive *S. cerevisiae* cells of strain AH109

| | IC$_{50}$ (μM) | | | | |
|---|---|---|---|---|---|
| fluconazole | itraconazole | ketoconazole | amphotericin B | ebselen | ebselen se-oxide |
| 53.00 | 1.13 | 0.54 | 0.03 | 4.60 | 2.10 |

FIG 2

Growth inhibitory effect of ebselen, ebselen se-oxide and standard antifungals upon fluconazole-resistant C. albicans cells of strain ATCC 96901

| | | | IC$_{50}$ (µM) | | |
|---|---|---|---|---|---|
| fluconazole | itraconazole | ketoconazole | amphotericin B | ebselen | ebselen se-oxide |
| >100 | 0.48 | 0.21 | 0.23 | 5.83 | 4.50 |

FIG 3

Minimal inhibitory concentration of fluconazole, ebselen and ebselen se-oxide determined using fluconazole-resistant *C. albicans* strains S2 and ATCC 96901

| *C. albicans* strain | MIC (μM) | | |
|---|---|---|---|
| | fluconazole | ebselen | ebselen se-oxide |
| S2 | >100 | 17.0 | 12.5 |
| ATCC 96901 | >100 | 12.5 | 12.5 |

FIG 4

Effect of ebselen and ebselen se-oxide on the activity of the yeast plasma membrane (H+)-ATPase

| IC50 (μM) | |
|---|---|
| ebselen | ebselen se-oxide |
| 3.0 | 3.8 |

FIG 5

| Effect of ebselen and ebselen se-oxide on the viability of A-431 human skin cells | |
|---|---|
| LC50 (µM) | |
| ebselen | ebselen se-oxide |
| >60 | >60 |

FIG 6

PROCESS FOR THE TREATMENT AND PREVENTION OF DISEASES CAUSED BY FUNGI

RELATED APPLICATIONS

This application claims benefit of provisional application No. 61/065,833, filed on Feb. 19, 2008.

BACKGROUND OF THE INVENTION

Introduction

Diseases such as cryptococcosis, aspergillosis, pneumonia, and systemic candidiasis represent a small sample of human pathologies caused by opportunistic fungi. All of these diseases can be life-threatening to immunocompromised patients, particularly among those with AIDS, those receiving chronic steroid regimens, or in patients whose immunity has declined as a result of aging (1,2). All systemic mycoses are serious in nature, and are considered medical emergencies.

Some of the most problematic fungal infections, also known as mycoses, are caused by various species of *Histoplasma, Cryptococcus, Aspergillus* and *Candida*. In particular, the genus *Candida* is comprised of approximately 200 species of yeasts, with *Candida albicans* (*C. albicans*) representing one of the major pathogenic species within the genus (3). *Candida* yeast cells are able to bind to inert surfaces such as the teflon tubing used in numerous medical devices, metharcylate, and the resin of artificial dentures (4). A high risk of invasive candidiasis has been linked to the use of vascular catheters and ventricular assistive devices. In a recent study, the probability of bloodstream infections resulting from colonization of *Candida* species on catheters ranked second to *Staphylococcus aureus* (5). *Candida* has been reported as the fourth most common cause of blood stream infection in the United States (6).

Current drug options to treat systemic mycoses are primarily aimed at disrupting critical yeast cell wall components or the biosynthetic pathway leading to ergosterol, two targets which are unique to yeast cells. In particular, the antifungal drug fluconazole has been found to be highly efficacious against opportunistic fungi. It should, however, be noted that fluconazole-resistant strains of fungi are emerging, and particularly among HIV patients infected with strains of *C. albicans* (7-9). The emergence of fluconazole-resistant strains of fungi points to the need for the immediate development of novel antifungal treatments.

Recent studies by this laboratory (10) and other investigators (11-14) have shown that the synthetic selenium-containing antioxidant ebselen, also referred to as 2-phenyl-1,2-benzisoselenazol-3(2H)-one (15), exhibits antifungal activity towards selected, fluconazole-sensitive strains of *Saccharomyces* (10,11) and *Candida* (11-13), as well as against a strain of *Cryptococcus* (11). The antifungal properties of ebselen in said strains results, at least in part, from its inhibition of a the yeast plasma membrane (H+)-ATPase pump, a vital enzyme used by yeast to establish proton gradients and maintain a proper intracellular pH (11,14). However, since it is common for yeast which are resistant to one antifungal drug to exhibit cross-resistance to other such drugs, the observations described herein, which reveal that ebselen and its analog ebselen se-oxide inhibit the growth of fluconazole-resistant yeast strains, are important observations which were not inherently obvious based upon the prior art.

Ebselen has been found to be useful for treating rheumatic diseases (15), treating diseases caused by oxidative stresses (16), and treating cataracts (17) and is produced in a highly pure form by a synthetic method which has been described previously (18). The compound is also commercially available from many different chemical vendors.

Ebselen se-oxide, also known as 2-phenyl-1,2-benzisoselenazol-3(2H)-one 1-oxide (19), is a synthetic compound which, unlike ebselen, contains a tetravalent selenium atom within the benzisoselenazol moiety of its molecular structure. Ebselen se-oxide is produced from the reaction of ebselen with peroxynitrite according to the process of H. Masumoto and H. Sies described in 1996 (19). Alternatively, ebselen se-oxide can be synthesized from ebselen using the procedure described by A. Welter (20). At the present time, this analog of ebselen is not commercially available.

The use of ebselen, as described below, to suppress the growth of drug-resistant fungi, such as *C. albicans* yeast cells exhibiting documented resistance to fluconazole, is novel to the art. The pharmacologic utility of ebselen se-oxide as an antifungal agent, through the inhibition of Pma1p, is also novel to the art of treating fungal diseases. Indeed, to the present date, none of the antifungal drugs approved for use in the United States achieves antifungal efficacy through a mechanism involving inhibition of the yeast plasma membrane (H+)-ATPase. Moreover, the tetravalent selenium atom of ebselen se-oxide (see Formula II) sets it apart from other benzisoselenazol-bearing compounds within the art.

The invention described here relates to a process for the treatment or prevention of fungal infections, particularly those in which fungi are resistant to fluconazole, using an effective amount of ebselen or the related chemical ebselen se-oxide. The invention is based on the observations presented in the Experimental Findings section of this application which reveal the antifungal effects of ebselen and ebselen se-oxide on clinical isolates of *C. albicans* exhibiting documented resistance to fluconazole (21,22).

SUMMARY OF THE INVENTION

This invention describes a process for the treatment of diseases caused by opportunistic fungal infections, particularly those that are resistant to standard antifungal therapy, in a wide variety of animals including premature neonates to adult humans and entails administering to said animal or human being a pharmaceutical preparation comprising of an effective amount of an agent that suppresses the activity of the fungal (H+)-ATPase pump (Pma1p). Such agents may take the form of 2-phenyl-1,2-benzisoselenazol-3(2H)-one, commonly referred to as ebselen and depicted by Formula I.

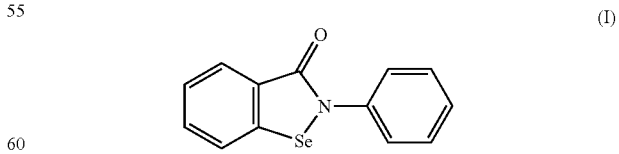

(I)

Such agents may also take the form of 2-phenyl-1,2-benzisoselenazol-3(2H)-one 1-oxide, also known by the alternate chemical name of 2-phenyl-1,2-benzisoselenazol-1,3-dione, and commonly referred to as ebselen se-oxide. The chemical structure of ebselen se-oxide is depicted by Formula II.

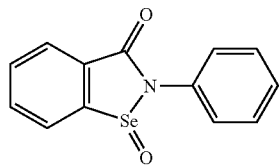

(II)

Administration of ebselen or ebselen se-oxide to treat superficial fungal infections may be performed via topical routes of administration, such as via an ointment, spray, eye drop solution, cream, mouth wash, soap or lotion. Administration of subject compounds to treat systemic mycoses may be performed by an intravenous route, a rectal route, an intranasal route, an oral route, an intramuscular route, or by inhalation. Ebselen or ebselen se-oxide may be administered alone, or with a carrier such as dimethysulfoxide (DMSO), an alcohol, or other suitable carrier. The effective daily amount of each of the said compounds is from about 1 μg/kg to 10 mg/kg of body weight. The dosages may be administered daily as a single dose or in several partial doses.

BRIEF DESCRIPTION OF FIGURES

FIG. 1: Atomic composition, chemical and generic names of the preferred benzisoselenazol-bearing compounds described herein FIG. 2: Growth inhibitory effect of ebselen, ebselen se-oxide and standard antifungals upon fluconazole-sensitive *S. cerevisiae* cells of strain AH109.

FIG. 3: Growth inhibitory effect of ebselen, ebselen se-oxide and standard antifungals upon fluconazole-resistant *C. albicans* cells of strain ATCC 96901.

FIG. 4: Minimal inhibitory concentration of fluconazole, ebselen and ebselen se-oxide determined using fluconazole-resistant *C. albicans* strains S2 and ATCC 96901.

FIG. 5: Effect of ebselen and ebselen se-oxide on the activity of the yeast plasma membrane (H+)-ATPase.

FIG. 6: Effect of ebselen and ebselen se-oxide on the viability of A-431 human skin cells.

DETAILED DESCRIPTION OF THE INVENTION

The subject invention is directed to the treatment of humans or animals afflicted by opportunistic fungal infections, particularly by fluconazole-resistant isolates of fungi, using a process which involves the administration of an effective amount of a compound capable of inhibiting the fungal plasma membrane (H+)-ATPase pump (Pma1p). The Pma1p inhibitor as the active agent is to be administered in an amount ranging from 1 to 1200 mg per day. The said ATPase pump, commonly referred to as Pma1p, is a vital enzyme in both unicellular and filamentous fungi and represents a new therapeutic target in the fight against human diseases caused by fungi. The invention has efficacy against drug-resistant fungi, as well as against fungi not known to be resistant to standard antifungal therapies. Drug-resistant fungi are those which have developed resistance to azoles, such as fluconazole, or to other standard antifungal agents currently in clinical use, such as drugs which can be structurally classified as polyenes or echinocandins. Opportunistic fungal infections include those which are systemic, in which the fungal pathogens have gained access to the circulatory system, and those which are superficial, in which the fungal pathogens are localized to a specific body compartment that is exposed to the environment such as the skin, the ears, the throat, the eyes, the lungs, the fingers, the fingernails, the toes, the toenails, the nose, the vagina, the penis, or the mouth. Examples of such opportunistic fungal infections include those caused by species of fungi belonging to the genus *Candida, Aspergillus, Pneumocystis, Tinea, Blastomyces, Cryptococcus, Histoplasma, Sporotrichum, Malassezia, Hansenula, Rhodotorula, Trichosporon*, as well as others.

The said invention provides for a treatment against opportunistic fungal infections and is intended for a variety of mammals, such as premature neonates to adult humans. Moreover, the said invention is useful in humans who are predisposed to fungal infections, such as those with immunodeficiency disorders and those who are immunosuppressed due to chemotherapy or other causes. In addition, the invention is intended for use in situations wherein the disease-causing pathogen is a fungus with documented resistance to fluconazole or to another antifungal agent that is currently in clinical use.

In the preferred embodiment of the invention, the compound capable of inhibiting the fungal Pma1p enzyme and treating the opportunistic fungal infection in mammals is ebselen (2-phenyl-1,2-benzisoselenazol-3(2H)-one), ebselen se-oxide (2-phenyl-1,2-benzisoselenazol-3(2H)-one 1-oxide), or a structurally-related chemical analog of said compounds. A structurally-related analog of ebselen or ebselen se-oxide is a chemical that bears a benzisoselenazol structural moiety in which the selenium atom of said structural moiety is either divalent or tetravalent in nature.

Administration of ebselen, ebselen se-oxide, or a structurally-related analog of said compounds to treat superficial fungal infections, also known as superficial mycoses, may be performed by a topical application, such as via an ointment, a spray, a cream, a mouth wash, an eye drop solution, an ear drop solution, a soap, or a lotion. In addition, an antifungal capsule can be administered orally or intravaginally. A water-soluble capsule with a soft gelatin shell is preferred type of capsule to be used for intravaginal administration.

Administration of ebselen, ebselen se-oxide, or a structurally-related analog of said compounds may also be used to treat systemic mycoses and, to this end, may be performed by an intravenous route, a rectal route, an intranasal route, an oral route, an intramuscular route, or by inhalation.

Ebselen, ebselen se-oxide, or a structurally-related analog of said compounds may be administered alone, or with a carrier such as DMSO, an alcohol, or other suitable carrier. Such carriers are well known in the art, and the specific carriers employed may be varied upon factors such as size of the subject being treated, treatment dose, and the like.

The effective daily amount of ebselen or ebselen se-oxide or an analog of said compounds having either a divalent or tetravalent selenium atom within its structure is from about 1 μg/kg to 10 mg/kg of body weight.

The dosages may be administered daily as a single dose or in several partial doses, up to 4 times daily, until the desired daily dosage is fully administered. The time frame over which the said compound is administered may vary as is well known in the art to achieve the desired results. For example, the said compound may be administered as an intravenous infusion from about 10 minutes to about 1 hour per treatment regimen, 3 or 4 times daily, or until the daily dosage is fully administered.

For the purpose of the invention, all forms of ebselen, ebselen se-oxide, or structurally-related chemical analogs of the said compounds, regardless of source, would follow a treatment similar to that described above.

The subject invention is also directed to the preventative treatment of infections by the fungi mentioned above. To this end, inhibitors of the fungal plasma membrane (H+)-ATPase may be utilized as prophylactic agents to prevent the development of fungal infections, particularly in immunosuppressed and immunocompromised human populations who are at high risk of such infections. In specific terms, prophylaxis against said fungal infections may be achieved by the administration of an effect amount of said inhibitors in the form of lotions, soaps, and creams.

The subject invention is also directed to the preservation of foods from spoilage by fungal microbes through the application of an effective amount of an inhibitor of the fungal (H+)-ATPase pump to the surface of fruits and vegetables. Application of said inhibitor can be achieved by spraying said fruit or vegetable with a solution containing between 0.1 and 50% of ebselen, ebselen se-oxide, or a structurally-related analog of said compounds.

The subject invention is also directed to the elimination of fungal mold infestations, such as those that result from damp conditions in homes and workplaces, through the application of an effective amount of an inhibitor of the fungal (H+)-ATPase pump to the infested area. Infested areas are those areas in which toxic fungal molds have accumulated to levels that can cause disease in humans. The application of said inhibitor to areas infested with fungal molds can be achieved by spraying a solution containing between 0.1 and 50% of said inhibitor. In the preferred embodiment of the invention, the compound capable of inhibiting the fungal Pma1p enzyme and treating the fungal mold infestation is ebselen, ebselen se-oxide, or a structurally-related chemical analog of said compounds.

Experimental Findings
Materials
Chemicals:

Samples of ebselen (Formula I) and ebselen se-oxide (Formula II) were purchased from Cayman Chemical (Ann Arbor, Mich.). FIG. 1 depicts the atomic composition, chemical and generic names of these two compounds. Note that ebselen se-oxide was prepared by Cayman Chemical as a custom synthesis, using the synthetic scheme of A. Welter (20), and is not commercially available. Unless otherwise indicated, all other chemicals used in the study were obtained from Sigma Chemical Company (St. Louis, Mo.). Bacto™ Tryptone, Bacto™ yeast extract and 40% filter-sterilized dextrose were obtained from Becton, Dickinson and Co. (Franklin Lakes, N.J.).

Yeast Strains:

The *S. cerevisiae* strain AH109 is a haploid yeast strain obtained from Clontech (Palo Alto, Calif.). *C. albicans* ATCC 96901 is a fluconazole-resistant strain obtained from the American Type Culture Collection (ATCC, Manassas, Va.). The ATCC 96901 strain of *C. albicans* is pathogenic and was originally isolated from an oral lesion of a patient with HIV (21). The S2 strain of *C. albicans*, also a fluconazole-resistant clinical isolate (22), was kindly provided by Dr. Joachim Morschhäuser (University of Wurzburg).

Skin Cells:

A-431 human epidermoid carcinoma cells were obtained from the American Type Culture Collection (ATCC, Manassas, Va.).

Culture Media:

YPD medium was prepared from Bacto™ Tryptone (20.0 g), Bacto™ yeast extract (10.0 g) and distilled water (950.0 mL), followed by adjustment of the pH to 6.5 with HCl. After autoclaving at 121° C. (15 min), the medium was supplemented with 40% filter-sterilized dextrose (50.0 mL) and 0.2% filter-sterilized adenine hemisulfate salt (15.0 mL). The YPD medium used for *C. albicans* culturing was supplemented with 0.7% (weight/volume) of adenine hemisulfate salt. RPMI-1640 broth medium (Lonza Walkersville, Inc., MD) with L-glutamine but without sodium bicarbonate, buffered at pH 7.0 with 0.165 M morpholinepropansulfonic acid (MOPS), was the medium used for broth dilution susceptibility testing of fluconazole-resistant *C. albicans* strains. Dulbecco's Modified Eagle's Medium (DMEM) containing L-glutamine, 4.5 mg glucose/L, and 10% heat-inactivated fetal bovine serum, supplemented with 50 µg/ml of gentamicin (complete DMEM), was used in the culturing of the human skin cells.

Drug Solutions:

Stock solutions of ebselen (100 mM), ebselen se-oxide (100 mM), fluconazole (16.32 mM) and ketoconazole (28.2 mM) were prepared in dimethylsulfoxide (DMSO). A solution of itraconazole (7.1 mM) was prepared in dimethylformamide (DMF); and one of amphotericin B (21.6 mM) in distilled water. In all of the experiments described below, the concentration of vehicle added did not exceed 0.1% (by volume). This concentration of vehicle did not affect the normal growth of the human skin cells or any of the yeast strains examined.

Methods

Comparison of Ebselen and Ebselen Se-Oxide with Standard Azole and Polyene Antifungal Agents for their Inhibitory Action on the Growth of *S. cerevisiae* Strain AH109 or *C. albicans* strain ATCC 96901:

AH109 cells or ATCC 96901 cells were inoculated into 200.0 ml of YPD to obtain an initial OD600 reading of 0.005 on a spectrophotometer. The yeast suspension was divided into 10.0 ml aliquots, to which a different concentration of ebselen (0.001-30.0 µM), ebselen se-oxide (0.001-30.0 µM), an azole compound (fluconazole, ketoconazole, itraconazole) (0.001-600.0 µM), or a polyene (amphotericin B) (0.001-1.0 µM) was added. The yeast suspensions were placed on a shaking incubator set at 200 rpm and 30° C. for 18-24 hr (*S. cerevisiae*) or 10-12 hr (*C. albicans*), and then the extent of fungal growth was assessed by measuring the sample absorbance at 600 nm (A600 nm) on a spectrophotometer. The effect of each concentration of antifungal agent was tested in triplicate.

Broth Microdilution Susceptibility Testing of *C. albicans:*

Note that all susceptibility assays were performed in triplicate wells using sterile flat-bottom 24-well microtiter plates. In brief, three to five colonies of *C. albicans* strains S2 or ATCC 96901 greater than 1 mm in diameter were selected from stock plates, suspended in RPMI, and adjusted to obtain an initial inoculum $OD_{600}$ nm of ~0.010 on a spectrophotometer. Stock solutions of ebselen or fluconazole were prepared in 100% dimethyl sulfoxide (DMSO) and then diluted 1:1000 in RPMI 1640 medium buffered to pH 7.0 with MOPS buffer to obtain the ×2 drug concentration (200 µM). Each well of the microplate containing 200 µl of the appropriate ebselen or fluconazole solution (2× final concentration) was inoculated with 200 µl of the inoculum suspension, yielding final fluconazole or ebselen concentrations ranging from 3.125 µM to 100 µM. The growth control wells each contained 200 µl of the diluted inoculum suspension, 200 µl of RPMI medium and 0.1% DMSO vehicle. Sterility control wells contained 400 µl of RPMI. After 48 (±30) hr of incubation at 30° C., the MIC (minimum inhibitory concentration) values for ebselen and fluconazole were determined visually by comparing the turbidity of the triplicate treatments to that observed for drug-free growth control wells. For each strain, the MIC was defined as the lowest concentration showing 100% growth inhibition, relative to controls, in all three wells of a given treatment.

Determination of the ATPase Activity of the Yeast Plasma Membrane (H+)-ATPase (Pma1p):

The effect of an organoselenium compound on ATPase activity was evaluated using a partially-purified sample of Pma1p from *S. cerevisiae* graciously provided by Dr. David Perlin, (The Public Health Research Institute Center, Newark, N.J.). This aim was accomplished by measuring the ATPase activity of Pma1p in the absence and presence of ebselen or ebselen se-oxide (1, 2, 3, 5, or 10 µM) by the method of Wang and colleagues (23). In these experiments, Pma1p was pre-incubated with each of the test compounds at 30° C. for 30 min before assessing its ATPase activity. The reaction medium used for this purpose, with or without an inhibitor, contained 10 mM of MES-Tris (pH 6.5), 5 mM of MgSO4, 25 mM of NH4Cl, 2 mM of ATP, 1-2 µg of partially-purified Pma1p, and 2% of dextrose. Further additions included 50 mM of KNO3 (to inhibit vacuolar ATPase), 0.2 mM of ammonium molybdate (to inhibit acid phosphatase) and 5 mM of NaN3 (to inhibit mitochondrial ATPase). The reaction was stopped after 15 min by adding the malachite green reagent. The green complex that formed between malachite green and free phosphate was measured with a microplate reader set at 630 nm.

Effect of Ebselen and Ebselen Se-oxide on the Viability of Human Skin Cells:

Confluent 24-well microtiter plates were used to examine the effects of ebselen or ebselen se-oxide on the viability of human A-431 skin cells. On the day cells were treated, media was removed from the wells and replaced with 0.5 ml of serum- and phenol red-free DMEM containing either 0 (control), 15, 30 or 60 µM of either ebselen or ebselen se-oxide. Cells were then incubated for 48 hr at 37° C. After incubation, the MTT viability assay was performed. This assay measures the conversion of 3-[4,5-dimethylthiazol-2-yl]-2,5-diphenyl tetrazolium bromide (MTT) into a colored product in living cells. The optical density of this purple formazan product in the cell culture medium was then measured spectrophotometrically at 570 nm and cell viability was determined as described by Mosmann (24).

Results

Comparison of the Growth Inhibitory Effect of Ebselen to that of Ebselen Se-oxide and other Standard Antifungal Agents upon *S. cerevisiae* and *C. albicans*:

To gauge the potency of ebselen and ebselen se-oxide as antifungal agents, the growth inhibitory action of these two selenocompounds was compared to that of currently used antifungals classified as azoles (fluconazole, ketoconazole, itraconazole) and polyenes (amphotericin B). For this purpose, *S. cerevisiae* strain AH109 and *C. albicans* strain ATCC 96901 were grown in YPD medium containing 0.0-100.0 µM of an antifungal agent, and the yeast growth assessed after 10-12 hr (*C. albicans* ATCC 96901) or 18-24 hr (AH109 cells) by measuring the turbidity of the culture medium on a spectrophotometer. Based on $IC_{50}$ values, the concentration of drug required to inhibit the growth of yeast cells by 50%, the antifungal potency against *S. cerevisiae* strain AH109 decreased in the order amphotericin B ($IC_{50}$=0.03 µM)>ketoconazole ($IC_{50}$=0.54 µM)>itraconazole ($IC_{50}$=1.13 µM)>ebselen se-oxide ($IC_{50}$=2.10 µM)>ebselen ($IC_{50}$=4.60)>fluconazole ($IC_{50}$=53.00 µM). On the other hand, when the test yeast was *C. albicans* the antifungal potency decreased in the order, ketoconazole ($IC_{50}$=0.21 µM)>amphotericin B ($IC_{50}$=0.23 µM)>itraconazole ($IC_{50}$=0.48 µM)>ebselen se-oxide ($IC_{50}$=4.50 µM)>ebselen ($IC_{50}$=5.83 µM)>fluconazole ($IC_{50}$=460.00 µM), respectively. These results are summarized in FIG. 2 and FIG. 3.

Evaluation of the Antifungal Activity of Ebselen and Ebselen Se-oxide in Yeast which are Resistant to Fluconazole:

While the molecular mechanism of azole resistance by *C. albicans* strain ATCC 96901 is unknown, the S2 strain is reported to be resistant to fluconazole, in part, because of the overexpression of several proteins, among them the drug efflux pump Mdr1p and several genes involved in ergosterol synthesis (22). Using this strain, as well as ATCC 96901, MIC values for ebselen, ebselen se-oxide and fluconazole in RPMI medium were obtained. Recall from above that the MIC is defined as the lowest concentration showing 100% growth inhibition, relative to controls, in all three wells of a given treatment. As can be seen in FIG. 4, ebselen and ebselen-oxide had more efficacy in vitro, as determined by their lower MIC values, than fluconazole against both fluconazole-resistant strains. These observations are novel to the art.

Assessment of the Effect of Ebselen and Ebselen Se-oxide on the Yeast Plasma Membrane H+-ATPase (Pma1p) Activity:

The Pma1p of fungi acts as an electrogenic proton pump that couples the hydrolysis of ATP to ion transport, specifically the transport of protons (H+). The effect of ebselen or ebselen se-oxide on this pump was tested using a partially-purified sample of Pma1p from *S. cerevisiae* following its pre-incubation with a test compound. In each instance, the activity was assessed based on the amount of inorganic phosphate released from ATP into the extracellular medium. Both of the test compounds showed an ability to reduce the activity of the partially-purified Pma1p in direct proportion to the amount of organoselenium compound present. As shown in FIG. 5, the yeast plasma membrane (H+)-ATPase was found to be sensitive to both ebselen ($IC_{50}$=3.0 µM) ebselen se-oxide ($IC_{50}$=3.8 µM). In this instance the $IC_{50}$ value represents the concentration of ebselen or ebselen se-oxide needed to reduce the activity of the yeast Pma1p by 50%.

Assessment of the Effect of Ebselen and Ebselen Se-Oxide on the Viability of Human Skin Cells:

To determine whether or not ebselen or ebselen se-oxide can exhibit a cytotoxic effect upon human cells, A-431 human skin cells were incubated at 37° C. for 48 hr in the absence or presence of 15, 30, or 60 µM of each respective compound. The MTT assay was used to determine cell viability and the $LC_{50}$ value for each compound was evaluated. Note that the $LC_{50}$ value represents the lethal concentration of an agent which kills 50% of the cell population. As shown in FIG. 6, neither compound was toxic to the skin cells over the range of concentrations tested.

Discussion

A series of microorganisms that included one strains of *S. cerevisiae*, and two strains of fluconazole-resistant *C. albicans* were used to evaluate the effect of ebselen and ebselen se-oxide on fungal growth. Both compounds were found to inhibit the nonpathogenic *S. cerevisiae* strain and the pathogenic *C. albicans* strains in the low micromolar range. In specific terms, these observations are new to the art and demonstrate that ebselen and ebselen se-oxide each effectively inhibit the growth of yeast strains resistant to fluconazole (FIG. 3 and FIG. 4). Furthermore, the ability of these compounds to inhibit the growth of fluconazole-resistant strain S2 demonstrates that ebselen and ebselen se-oxide work as effective antifungal agents despite the upregulation in these yeast of Mdr1p and several other genes involved in ergosterol synthesis (22).

While the mechanism of the antifungal activity of ebselen and ebselen se-oxide remains unclear, the present data show that these compounds inhibit of the fungal plasma membrane H+-ATPase at the low micromolar concentrations (FIG. 5). In fungi, this pump plays important roles in regulating intracellular pH and maintaining electrochemical proton gradients necessary for nutrient uptake (25). It is noteworthy that the concentration of ebselen or of ebselen se-oxide which was required to inhibit the growth of AH109 or ATCC 96901 cells by 50% was roughly the same as that needed to strongly inhibit the yeast plasma membrane (H+)-ATPase. Furthermore, ebselen se-oxide, an analog of ebselen bearing a tetravalent selenium atom, was about equipotent to ebselen in terms of Pma1p inhibitory power. The observation that a compound bearing a tetravalent selenium atom within the benzisoselenazol moiety of its structure can exhibit antifungal activity has, to my knowledge, not been reported elsewhere.

The similarity in antifungal activity between the ebselen se-oxide and ebselen might be a consequence of the conversion of ebselen se-oxide to ebselen following its uptake into a fungal cell. In other words, ebselen se-oxide may be acting as an ebselen prodrug. To the present date, neither the antifungal activity of ebselen se-oxide nor the use of an ebselen prodrug to combat fungal infections has been reported in the scientific literature. Moreover, it is likely that other benzisoselenazol-bearing chemicals in which the selenium atom is tetravalent will also possess strong antifungal activity, as was observed here for ebselen se-oxide.

To gain an insight as to whether or not ebselen or its se-oxide can negatively impact the viability of human cells, viability studies were performed using A-431 human skin cells that were incubated with increasing concentrations of these agents. The viability of skin cells was not found to be affected by concentrations of either compound well above that needed for antifungal efficacy (FIG. 6). Based on these observations, it is concluded that ebselen and ebselen se-oxide can be used in the treatment of fungal diseases at concentrations which are toxic to fungi but not toxic to human cells.

In summary, ebselen and ebselen se-oxide have been found to have antifungal efficacy towards both pathogenic and non-pathogenic strains of yeast through a mechanism that targets the fungal plasma membrane H+-ATPase while not exhibiting toxicity towards human cells. Although ebselen and ebselen se-oxide appear to be less potent antifungal agents than several azole and polyene compounds in current clinical use they, however, show better activity than fluconazole against two fluconazole-resistant strains of *C. albicans*. Therefore, based on the studies reported here, it is reasonable to consider the Pma1p of yeast as a viable target for future antifungal agents and ebselen and its oxide analog as antifungals with strong potential for clinical use against fluconazole-resistant yeasts.

REFERENCES

1. Shao P L, Huang L M, Hsueh P R. Invasive fungal infection—laboratory diagnosis and antifungal treatment. J Microbiol Immunol Infect 2006; 39:178-188.
2. Clark T A, Hajjeh R A. Recent trends in the epidemiology of invasive mycoses. Curr Opin Infect Dis 2002; 15:569-574.
3. Segal E, Baum G. Pathogenic yeasts and yeast infections. CRC Press, Inc; Boca Raton, Fla., 1994.
4. Sanglard D, Ischer F, Parkinson T, Falconer D, Bille J. *Candida albicans* mutations in the ergosterol biosynthetic pathway and resistance to several antifungal agents. Antimicrob Agents Chemother. 2003; 47:2404-2412.
5. Khot P D, Suci P A, Miller R L, Nelson R D, Tyler B J. A small subpopulation of blastospores in *C. albicans* biofilms exhibit resistance to amphotericin B associated with differential regulation of ergosterol and beta-1,6-glucan pathway genes. Antimicrob Agents Chemother. 2006; 50:3708-3716.
6. McIlhatton B P, Keating C, Curran M D, McMullin M F, Barr J G, Madrigal J A, et al. Identification of medically important pathogenic fungi by reference strand-mediated conformational analysis (RSCA). J Med Microbiol. 2002; 51:468-478.
7. Rex J H, Rinaldi M G, Pfaller M A. Resistance of *Candida* species to fluconazole. Antimicrob Agents Chemother 1995; 39:1-8.
8. Collin B, Clancy C J, Nguyen M H. Antifungal resistance in non-albicans *Candida* species. Drug Resist Updat 1999; 2:9-14.
9. Johnson E M, Warnock D W, Luker J, Porter S R, Scully C. Emergence of azole drug resistance in *Candida* species From HIV-infected patients receiving prolonged fluconazole therapy for oral candidosis. J Antimicrob Chemother 1995; 35:103-114.
10. Chan G, Hardej D, Santoro M, Lau-Cam C, Billack B. Evaluation of the antimicrobial activity of ebselen: role of the yeast plasma membrane H$^+$-ATPase. J Biochem Mol Toxicol 2007; 21:252-264.
11. Soteropoulos P, Vaz T, Santangelo R, Paderu P, Huang D Y, Tamas M J, et al. Molecular characterization of the plasma membrane H(+)-ATPase, an antifungal target in *Cryptococcus neoformans*. Antimicrob Agents Chemother 2000; 44:2349-2355.
12. Bien M, Blaszczyk B, Kalinowska K, Mlochowski J, Inglot A D. Antifungal activity of 2-(4-chlorophenyl)-1,2-benzisoselenazol-3(2H)-one, the analog of ebselen. Arch Immunol Ther Exp (Warsz) 1999; 47:185-193.
13. Wojtowicz H, Kloc K, Maliszewska I, Mlochowski J, Pietka M, Piasecki E. Azaanalogues of ebselen as antimicrobial and antiviral agents: synthesis and properties. Farmaco 2004; 59:863-868.
14. Perlin D, Seto-Young D, Monk B. The plasma membrane H(+)-ATPase of fungi. A candidate drug target? Ann NY Acad Sci 1997; 834:609-617.
15. U.S. Pat. No. 4,352,799; inventors: Marcel Renson, Eugen Etschenberg, Johannes Winkelmann; issued 5 Oct. 1982
16. U.S. Pat. No. 4,757,063; inventor: Michael Parnham; issued 12 Jul. 1988
17. U.S. Pat. No. 4,778,815; inventor: William D. Cash; issued 18 Oct. 1988
18. U.S. Pat. No. 5,008,394; inventors: Bernd-Rainer Gunther, Rainer Losch, Klaus Steiner; issued 16 Apr. 1991
19. Masumoto H, Sies H. The reaction of ebselen with peroxynitrite. Chem Res Toxicol 1996; 9:262-267.
20. German Patent 3444135 A1; inventors: Andre Welter, Michael Parnham, Hartmut Fischer, Reinhardt Niemann, Peter Kuhl, Sigurd Leyck; issued 6 May 1986
21. Boken D J, Swindells S, Rinaldi M G. Fluconazole-resistant *Candida albicans*. Clin Infect Dis 1993; 17:1018-1021.
22. Dunkel N, Liu T T, Barker K S, Homayouni R, Morschhauser J, Rogers, P D. Gain-of-function mutation in the transcription factor Upc2p causes upregulation of ergosterol biosynthesis genes and increased fluconazole resistance in a clinical *Candida albicans* isolate. Eukaryot Cell 2008; 7:1180-1190.

23. Wang G, Tamas M J, Hall M J, Pascual-Ahuir A, Perlin D S. Probing conserved regions of the cytoplasmic LOOP1 segment linking transmembrane segments 2 and 3 of the *Saccharomyces cerevisiae* plasma membrane H+-ATPase. J Biol Chem 1996; 271:25438-25445.
24. Mosmann T. Rapid colorimetric assay for cellular growth and survival: application to proliferation and cytotoxicity assays. J Immunol Methods 1983; 65:55-63.
25. Serrano, R. (1988). Structure and function of proton translocating ATPase in plasma membranes of plants and fungi. Biochim Biophys Acta 1988; 947:1-28.

What is claimed is:

1. A method for treating a fungal infection caused by *Candida albicans* comprising the administration to a mammal of an effective amount of an inhibitor of the fungal plasma membrane (H+)-ATPase pump which is ebselen se-oxide (2-phenyl-1,2- benzisoselenazol-3(2H)-one 1-oxide).

2. A method of claim 1, wherein the mammal is a human neonate, a human adult, an immunosuppressed human, an immunocompromised human, a common farm animal or a common household pet.

3. A method of claims 1 or 2, wherein the fungal infection is caused by *Candida albicans* exhibiting resistance to antifungal agents which are classified chemically as echinocandins, imidazoles, triazoles or polyenes.

4. A method of claim 1, wherein administration to a mammal of an effective amount of an inhibitor of the fungal plasma membrane (H+)-ATPase pump is performed topically in the form of a cream, a gel, a lotion, an ointment, a foot spray, a nasal spray, a mouth wash rinse, an eye drop solution, a medicated shampoo, a soap, a douche, or an ear drop solution, or performed orally in the form of a tablet, a capsule, or a liquid, or performed intravaginally as a capsule, or performed intratracheally by nebulization, or performed intravenously by infusion, or performed subcutaneously, or intrathecally, by injection.

5. A method for treating a fungal infection caused by *Candida albicans* through the application of an effective amount of ebselen se-oxide (2-phenyl-1,2- benzisoselenazol-3(2H)-one 1-oxide) to medical instruments, medical devices, pharmaceuticals, or vaccines which are routinely inserted into body cavities, ducts or vessels.

6. A method of claim 5, wherein medical instruments include those used by gynecologists, dentists, otolaryngologists and gastroenterologists.

* * * * *